United States Patent
Chen (10) Patent No.: US 8,115,481 B2
(45) Date of Patent: Feb. 14, 2012

(54) METHOD OF DISCERNING WATER FROM HYDROCARBON FLUIDS USING DOWNHOLE NMR INSTRUMENTS IN PETROLEUM RESERVOIRS WITH FORMATION BRINE

(75) Inventor: Songhua Chen, Katy, TX (US)

(73) Assignee: Baker Hughes Incorporated, Houston, TX (US)

(*) Notice: Subject to any disclaimer, the term of this patent is extended or adjusted under 35 U.S.C. 154(b) by 272 days.

(21) Appl. No.: 12/177,246

(22) Filed: Jul. 22, 2008

(65) Prior Publication Data

US 2009/0179636 A1   Jul. 16, 2009

Related U.S. Application Data

(60) Provisional application No. 60/951,293, filed on Jul. 23, 2007.

(51) Int. Cl.
*G01V 3/00* (2006.01)
*G01R 33/20* (2006.01)

(52) U.S. Cl. .......................... 324/303; 324/306
(58) Field of Classification Search .......... 324/300–307, 324/314, 318–322; 382/128–131
See application file for complete search history.

(56) References Cited

U.S. PATENT DOCUMENTS

| | | | |
|---|---|---|---|
| 3,456,183 A * | 7/1969 | Codrington et al. | 324/303 |
| 3,528,000 A * | 9/1970 | Schwede | 324/303 |
| 4,710,713 A | 12/1987 | Strikman | |
| 5,619,138 A * | 4/1997 | Rourke | 324/309 |
| 5,712,566 A | 1/1998 | Taicher et al. | |
| 6,184,681 B1 * | 2/2001 | Heidler et al. | 324/303 |
| 6,246,236 B1 * | 6/2001 | Poitzsch et al. | 324/303 |
| 6,291,995 B1 * | 9/2001 | Speier et al. | 324/303 |
| 6,489,872 B1 | 12/2002 | Fukushima et al. | |
| 6,828,892 B1 | 12/2004 | Fukushima et al. | |
| 6,856,132 B2 * | 2/2005 | Appel et al. | 324/303 |
| 6,891,369 B2 * | 5/2005 | Hurlimann et al. | 324/303 |
| 2004/0090230 A1 * | 5/2004 | Appel et al. | 324/307 |
| 2009/0179636 A1 * | 7/2009 | Chen | 324/303 |

OTHER PUBLICATIONS

Manz, et al. "A mobile one-sided NMR sensor with a homogeneous magnetic field: The NMR-MOLE". Journal of Magnetic Resonance 183 (2006) 25-31.

* cited by examiner

*Primary Examiner* — Melissa Koval
*Assistant Examiner* — Tiffany Fetzner
(74) *Attorney, Agent, or Firm* — Cantor Colburn LLP (57) ABSTRACT

A method for analytically separating properties of hydrocarbon materials from other materials in a downhole environment, the method including: performing nuclear magnetic resonance (NMR) measurements downhole; determining a signal for sodium-23 ($^{23}$Na) from the NMR measurements; and associating the $^{23}$Na signal with the other materials. A computer program product, an apparatus and additional methods are provided.

18 Claims, 4 Drawing Sheets

METHOD OF DISCERNING WATER FROM HYDROCARBON FLUIDS USING DOWNHOLE NMR INSTRUMENTS IN PETROLEUM RESERVOIRS WITH FORMATION BRINE

CROSS REFERENCE TO RELATED APPLICATION

The present application is filed under 37 CFR §1.53(b) and 35 U.S.C. §120 and claims priority to U.S. Provisional Patent Application Ser. No. 60/951,293, filed Jul. 23, 2007, the entire contents of which are specifically incorporated herein by reference in their entirety

BACKGROUND OF THE INVENTION

1. Field of the Invention

The invention disclosed herein relates to geophysical assessments using nuclear magnetic resonance techniques and, in particular, to techniques for discerning water from hydrocarbon fluids.

2. Description of the Related Art

Many petroleum reservoirs around the world contain salty formation water. Formation water can be of meteoric or connate origin, or from a mixture of both. Although seawater contains salt of about 30 kppm, the average petroleum reservoir having connate brine contains about 80 kppm of salt. Many petroleum reservoirs that are saturated with salt, such as those common to the major oil-producing or gas-producing fields in the Middle East, contain salt as high as 250 kppm, (i.e., the salt may represent up to about 25% of the weight of the brine). Connate brine contains mainly NaCl salt.

Current NMR wireline and logging techniques only use measurements for protons for a good reason. The proton has a natural abundance of nearly 100%. In addition, the proton has the strongest per-sample signal intensity, as determined by $f_0^3 I(I+1)$, where $f_0$ is the NMR frequency and I is the spin quantum number. Because both the hydrocarbon phase and water (brine) phase contain protons, properties of each phase can not be determined from the proton signal intensity alone. Accordingly, the capability of traditional proton NMR techniques for discerning hydrocarbon from salty water downhole has its limitations.

Further, since brine is a conductive liquid, its presence in the formation has a negative effect on the signal quality of many other logging instruments, considering those instruments that are based on the transmitting and receiving of electrical power. Such instruments may include, but are not limited to, nuclear magnetic resonance (NMR) logging instruments and galvanic and inductive logging devices. Poor signal to noise ratio in a salty environment makes it even more difficult to discern hydrocarbon from water.

The current arts of NMR logging techniques discern hydrocarbon from brine based on their contrast in relaxation times (i.e., the longitudinal relaxation time $T_1$ and the transverse relaxation time $T_2$) and the fluid diffusivities, D. Although these techniques have been used successfully downhole, the applicability of these approaches relies heavily on the robustness of these contrasts and the adequate signal-to-noise ratio (SNR). For light hydrocarbons such as volatile and very low-viscosity oils, the water and oil diffusivity contrast is very small; it would be very difficult to separate oil and water from NMR responses, especially in the rocks with large pores and in vuggy carbonates.

On the other hand, determination of formation water resistivity is an important step for induction or resistivity-based saturation estimates. Although in many mature reservoirs the Rw value is well known, for exploration wells, it is important to be able to determine formation resistivity or the equivalent of formation water salinity.

The poor signal-to-noise ratio (SNR) and the possibility of mixing $^{23}Na$ signals from borehole with signals from protons (i.e., hydrogen) in formation fluids have been the main reason for not considering $^{23}Na$ NMR logging measurements using the current NMR logging instrument configurations.

Therefore, what are needed are techniques for discerning a presence of hydrocarbon materials from salty water downhole. Preferably, the techniques may be implemented using existing technologies, such as instruments using nuclear magnetic resonance (NMR).

BRIEF SUMMARY OF THE INVENTION

Disclosed is a method for analytically separating properties of hydrocarbon materials from other materials in a downhole environment, the method including: performing nuclear magnetic resonance (NMR) measurements downhole; determining a signal for sodium-23 ($^{23}Na$) from the NMR measurements; and associating the $^{23}Na$ signal with the other materials.

Also disclosed is a computer program product including machine readable instructions stored on machine readable media, the instructions for analytically separating properties of hydrocarbon materials from other materials in a downhole environment, by implementing a method including: performing nuclear magnetic resonance (NMR) measurements downhole; determining a signal for sodium-23 ($^{23}Na$) from the NMR measurements; and associating the $^{23}Na$ signal with the other materials.

Further disclosed is an apparatus for performing nuclear magnetic resonance (NMR) measurements in a wellbore, the apparatus including: a magnet configuration adapted for separating a proton response from a sodium-23 ($^{23}Na$) response for the NMR measurements.

Also provided is a method for analytically separating properties of hydrocarbon materials from other materials in a downhole environment, the method including: performing a first nuclear magnetic resonance (NMR) measurement for sodium-23 ($^{23}Na$) at a resonance frequency within a window of homogeneous magnetic field; performing a second nuclear magnetic resonance (NMR) measurement for hydrogen ($^1H$) at another resonance frequency within a window of homogeneous magnetic field; determining a signal for the $^{23}Na$ from the first NMR measurement; determining another signal for the $^1H$ and the $^{23}Na$ from the second NMR measurement; and separating the signal and the another signal to determine the properties of the hydrocarbon materials from the other materials.

Another embodiment of the invention includes a method for determining formation salinity variation when the oil and brine proton NMR response can be discerned from proton NMR measurements, the method including: performing proton and sodium nuclear magnetic resonance (NMR) measurements within a wellbore penetrating the formation; determining oil-filled and brine-filled porosity volumes separately with proton NMR parameters including at least one of a relaxation time, and a diffusivity, determining a magnitude of a sodium-23 ($^{23}Na$) NMR signal which represents brine, where the $^{23}Na$ NMR signal amplitude is pre-calibrated against a known salinity brine source; determining the salinity of brine from a ratio of magnitude of $^{23}Na$ signal and the brine filled porosity volume; where a variation of salinity as a function of measured depth along the bore hole is an indicator of at least one of mud filtrate invasion change and variation in native formation water salinity.

In addition, a method for determining water saturation in a formation is provided and includes: performing nuclear magnetic resonance (NMR) measurements within a wellbore penetrating the formation; determining a signal for sodium-23 ($^{23}$Na) from the NMR measurements; and using a known salinity for the water, determining water saturation in the wellbore from the signal.

BRIEF DESCRIPTION OF THE DRAWINGS

The subject matter which is regarded as the invention is particularly pointed out and distinctly claimed in the claims at the conclusion of the specification. The foregoing and other features and advantages of the invention are apparent from the following detailed description taken in conjunction with the accompanying drawings in which:

FIG. 4A and FIG. 4B, collectively referred to as FIG. 4, depicts relative sensitive volumes location of sodium and proton at a same resonance frequency and the shift of the sensitive volumes as the result of the frequency being shifted slightly.

DETAILED DESCRIPTION OF THE INVENTION

The teachings herein take advantage of various unique nuclear magnetic resonance (NMR) properties of sodium-23 ($^{23}$Na) to provide for separate determination of properties of water and hydrocarbon fluids when the water and hydrocarbon fluids reside downhole.

For perspective, this disclosure provides a review of techniques for well logging using nuclear magnetic resonance (NMR) technology; some background on NMR measurements and analyses; and, embodiments for using a $^{23}$Na signal for separation of water and hydrocarbon fluids.

As discussed herein, the term "separation" generally refers to analytical separation of properties associated with water, brine and other such fluids from the properties of hydrocarbons downhole. Separation is generally not meant to imply refining of mixtures of water, brine and hydrocarbon fluids such that physical separation is achieved. Rather, the term "separation" generally implies successful determination of properties, such that a user of the technology determines some benefit has been achieved. Prior to considering aspects of the teachings herein, aspects of geophysical exploration using nuclear magnetic resonance (NMR) technology is provided. The terms "water," "brine," and other such terms are generally related to fluids and other materials that are found downhole and that do not include hydrocarbon materials, or at least appreciable quantities of hydrocarbon materials. The term "proton" generally makes reference to protons bound in hydrogen, whether included in water or hydrocarbon materials.

Figure 1:
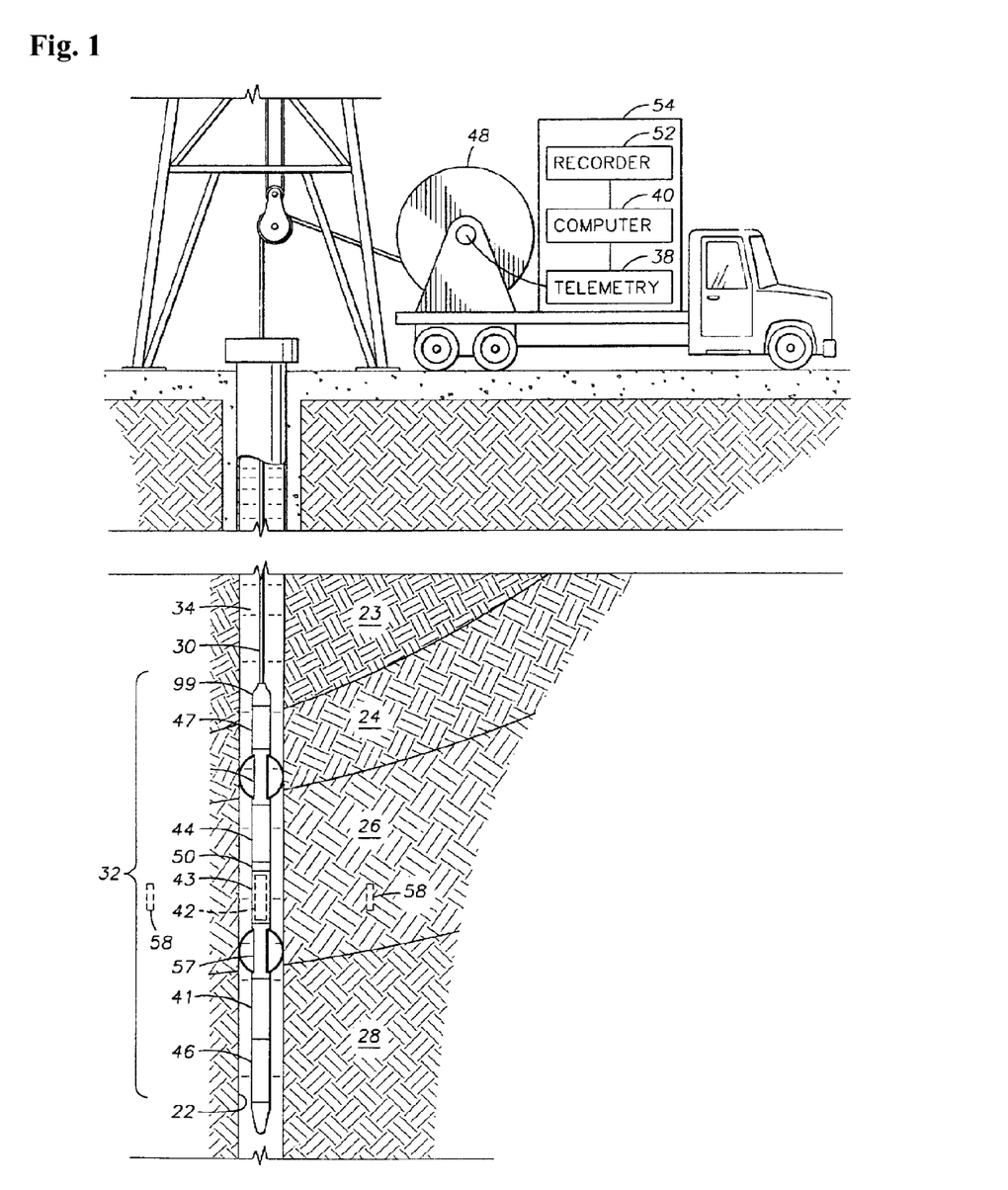
FIG. 1 depicts aspects of well logging with an nuclear magnetic resonance (NMR) apparatus.

Turning to FIG. 1, consider aspects of downhole NMR characterizations, using a non-limiting embodiment of a wireline logging device. One skilled in the art will recognize that the techniques disclosed herein can be applied with other embodiments, such as logging-while-drilling (LWD) or measurements-while-drilling (MWD) operations.

FIG. 1 shows a well logging apparatus disposed in a wellbore 22 penetrating earth formations 23, 24, 26, 28 for making measurements of properties of the earth formations 23, 24, 26, 28 downhole. The wellbore 22 in FIG. 1 is typically filled with a fluid 34 known in the art as "drilling mud." A "sensitive volume," shown generally at 58 and whose shape may vary due to different magnet designs, is disposed in one of the earth formations, shown at 26. The sensitive volume 58 is a predetermined portion of the earth formations 26 in which nuclear magnetic resonance (NMR) measurements are made, as will be further explained.

In typical embodiments, the sensitive volume 58 includes materials such as would be found downhole (below the surface and within or around the wellbore 22) including a mixture of fluids including gas, water, drilling fluid, oil and formation fluids that are indigenous to the formations 23, 24, 26, 28.

A string of logging tools 32, which can include an NMR apparatus according to the present invention, is typically lowered into the wellbore 22 by, for example, an armored electrical cable 30. The cable 30 can be spooled and unspooled from a winch or drum 48. The tool string 32 can be electrically connected to surface equipment 54 by an insulated electrical conductor (not shown separately in FIG. 1) forming part of the cable 30. The surface equipment 54 can include one part of a telemetry system 38 for communicating control signals and data to the tool string 32 and computer 40. The computer may also include a data recorder 52 for recording measurements made by the apparatus and transmitted to the surface equipment 54. Typically, the computer includes a variety of input/output devices and other supporting devices to enhance the operation of the apparatus and estimations performed by use thereof. An NMR probe 42 can be included in the tool string 32.

Circuitry for operating the NMR probe 42 can be located within an NMR electronics cartridge 44. The circuitry can be connected to the NMR probe 42 through a connector 50. The NMR probe 42 is typically located within a protective housing 43 which is designed to exclude the drilling mud 34 from the interior of the probe 42. The function of the probe 42 will be further explained.

Other well logging sensors (not shown separately for clarity of the illustration in FIG. 1) may form part of the tool string 32. As shown in FIG. 1, one additional logging sensor 47 may be located above the NMR electronics cartridge 44. Other logging sensors, such as shown at 41 and 46 may be located within or below the bottom centralizer 57. The other sensors 41, 46, 47 can be of types familiar to those skilled in the art.

Other aspects of the exemplary embodiment of the NMR probe 42 are provided in U.S. Pat. No. 5,712,566, entitled "Nuclear Magnetic Resonance Apparatus and Method," issued Jan. 27, 1998 to Taicher et al., and incorporated herein by reference in it's entirety. Another non-limiting example is disclosed in U.S. Pat. No. 4,710,713, also issued to Taicher et al, and also incorporated by reference herein in it's entirety. It should be recognized that these embodiments of NMR tools are exemplary only, and not limiting of the teachings herein. A commercially available and exemplary embodiment of an NMR instrument is the MREX™, available from Baker Hughes, Incorporated of Houston Tex.

One skilled in the art will recognize that while the teachings herein may be performed downhole, they are also applicable to evaluations conducted on the surface, such as in a laboratory. Further, and as discussed elsewhere herein, at least a portion of an evaluation or determination may be performed in one place or another. For example, a property of a constituent may be determined in a laboratory, while other measurements and determinations are performed downhole.

As a matter of convention, one should note that the variables used herein appear throughout the disclosure. Accordingly, previously defined variables are generally not reintroduced. For convenience of referencing, the following representations are some of the definitions applied herein, or related to the teachings herein: $B_0$ represents static field strength for a magnetic field; $B_1$ represents radiofrequency (RF) field strength; D represents diffusivity; f represents a proton fraction; G represents RF field gradient strength; R represents a resistivity; r represents a radius from a center of the wellbore; M represents echo magnetization amplitude; where $M_z(t)$ represents a longitudinal magnetization, which involves a time constant $T_1$, where $T_1$ is the time required for the magnetization vector to be restored to 63% of its original amplitude (referred to as "longitudinal relaxation time"); $M_{xy}$ represents a transverse magnetization, which involves a time constant $T_2$, where $T_2$ is the time required for the magnetization vector to drop to 37% of its original amplitude (referred to as "transverse relaxation time"); and $T_w$ represents a relaxation wait time.

A variety of techniques are provided herein for using an NMR signal associated with sodium-23 ($^{23}$Na) to provide for analytical separation of hydrocarbon materials from non-hydrocarbon materials downhole.

A first technique involves taking advantage of the relaxation time for $^{23}$Na. At a given field strength, the nominal $^{23}$Na NMR signal intensity is 0.0925 that of the proton. For very conductive samples, such as that of salt-saturated reservoirs, the relative sensitivity of $^{23}$Na, computed from $f_0^2 I(I+1)$, is about 0.35. Thus, it is favorable to apply the sodium NMR measurements in those salty wells. First, the signal for $^{23}$Na is strong. Secondly, the relative sensitivity to $^{23}$Na in comparison to protons is better than that in resistive media. Compared to proton relaxation times, $^{23}$Na NMR for NaCl solution is a few orders of magnitude shorter, (e.g., in a range of about 10 milliseconds compared to a range in seconds for protons). Therefore, the magnetization time for $^{23}$Na may be considered "substantially shorter" than the magnetization polarization time for the protons. Therefore, in a given amount of time, a substantial number of repetitive experiments can be performed to improve the SNR of $^{23}$Na measurements. This provides a basis for at least statistically overcoming the small signal intensity associated with $^{23}$Na. The capability of conducting quick and repetitive measurements can result in up to a ten fold of SNR improvement for sodium NMR for a single frequency measurement. Advantageously, because of the short relaxation time of $^{23}$Na, it is not important to have a long pre-polarization magnet.

Another technique for using the NMR signal associated with $^{23}$Na calls for using a magnet configuration that provides a large sensitive volume. Since the inception of NMR logging, concerns were raised of possible interference of $^{23}$Na signal from salt-saturated borehole mud fluid to interfere with proton NMR signal from the formation fluid. For gradient field NMR instruments such as MREX™, the signal associated with $^{23}$Na and obtained in the borehole has been proven too weak to be of use. The tiny sensitive volume, unfavorable tip angles, and the small relative intensity of $^{23}$Na, have all contributed to the absence of a $^{23}$Na signal in the proton NMR data.

Figure 2A:
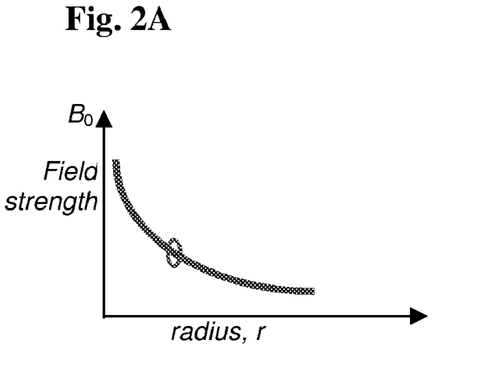
FIG. 2A and FIG. 2B, collectively referred to herein as FIG. 2, depict sensitive volumes in a gradient magnetic field.
Figure 2B:
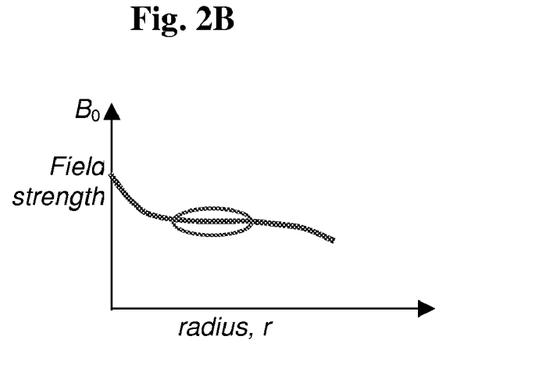

However, for a different configuration of magnet, such as a barrel magnet or a combination of barrel and bar magnet 400 (reference may be had to FIG. 5), a substantially large window of relatively homogeneous magnetic field, often called the "sweet spot," can be achieved. Thus, it is possible to select the $^{23}$Na resonance frequency such that the NMR sensitive volume falls into the sweet spot. The large sensitive volume increases the NMR signal strength, and compensates for the lower relative intensity of the NMR measurement for $^{23}$Na. A difference in the sensitive volume between the gradient magnetic field used in the MREX configuration is illustrated in FIG. 2A. In FIG. 2B, a barrel and bar magnet configuration is depicted. The curves provided in FIG. 2 are useful for depicting aspects of prior art instruments (e.g., MRIL tool by Halliburton Corporation of Houston Tex. and MREX tool by Baker Hughes Inc.) and embodiments of the teachings herein (e.g., use of a barrel-shaped magnet).

Exemplary barrel magnets 400 and combinations of barrel and bar magnets 400 are described in U.S. Pat. Nos. 6,489,872 and 6,828,892 by Fukushima and Jackson, respectively. The disclosures of these patents are incorporated herein by reference in their entirety. Other configurations for magnets may be used. As an example, magnet configurations provided in the MAGTRAK design of Baker Hughes, Incorporated may be used.

Figure 5:
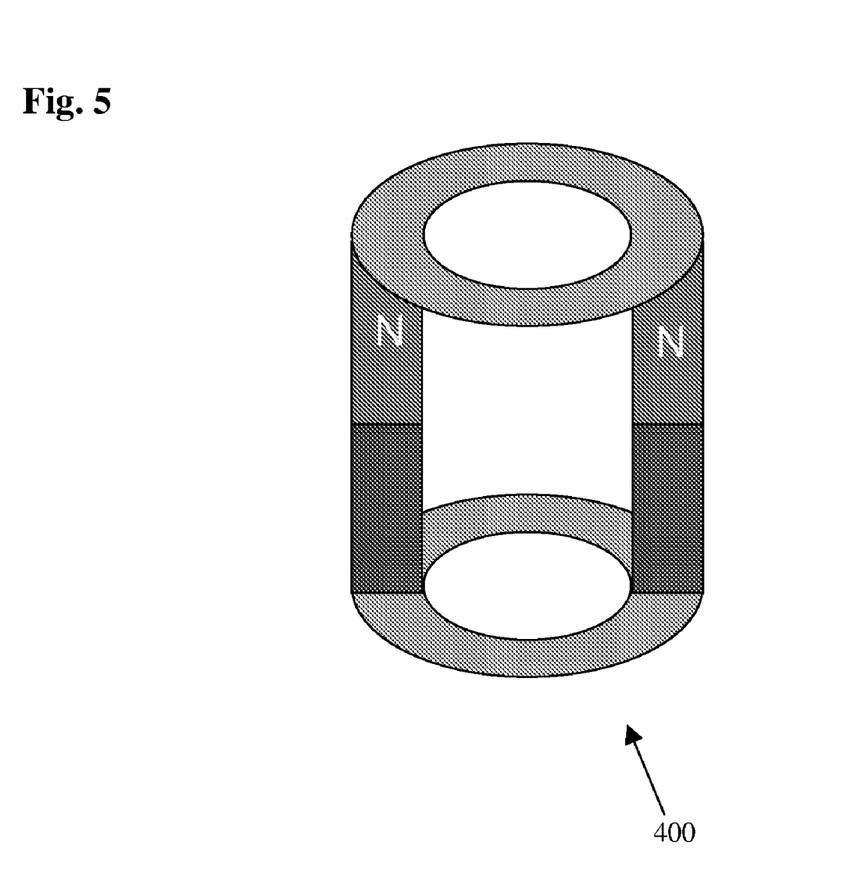
FIG. 5 depicts an embodiment of a magnet suited for practicing the teachings herein.

Use of a barrel magnet 400 and other similar configurations provides certain advantages. For example, one advantage of the barrel-shaped magnet configuration for $^{23}$Na NMR is that the signal is further away from the borehole, which is a large source of error in measurements for sodium.

Using these design principles, the volume of a relatively homogeneous magnetic field strength at the sweet spot is larger than in other traditional designs. Thus, more nuclei are included in the volume resulting in the stronger $^{23}$Na. Comparison may be made to CMR or NMR Mole (Manz et al, Journal of Magn Reson, v. 183 (2006)) designs, the barrel shaped magnet 400 has a stronger magnetic strength at the sweet spot. The improved magnetic strength, coupled with the large sensitive volume, further make the $^{23}$Na measurement practical.

In a further technique for using an NMR signal associated with sodium-23 ($^{23}$Na) to provide for analytical separation of hydrocarbon materials from non-hydrocarbon materials downhole, measurements may be performed where a shift to a resonance frequency that is off of the sweet spot is performed. Shifting of the resonance frequency provides for verification of any $^{23}$Na signals.

Figure 3:
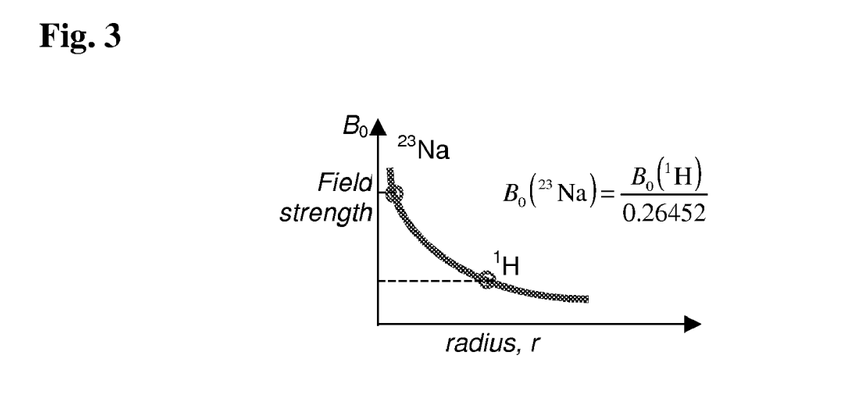
FIG. 3 depicts a shift of sensitive volume location along the radial direction from the NMR tool, under a given operation frequency excitation.

FIG. 3 depicts a shift of sensitive volume location along the radial direction from the NMR tool, under a given operation frequency excitation. Since $^{23}$Na has a smaller gyromatic ratio than that of protons, the sensitive volume is much closer to the borehole than that of protons.

The larger sensitive volume is only one of the advantages of the barrel magnet for $^{23}$Na NMR measurements. At a given resonance frequency, the magnetic field strength for $^{23}$Na to reach resonance condition is about four times that of protons.

Figure 4A:
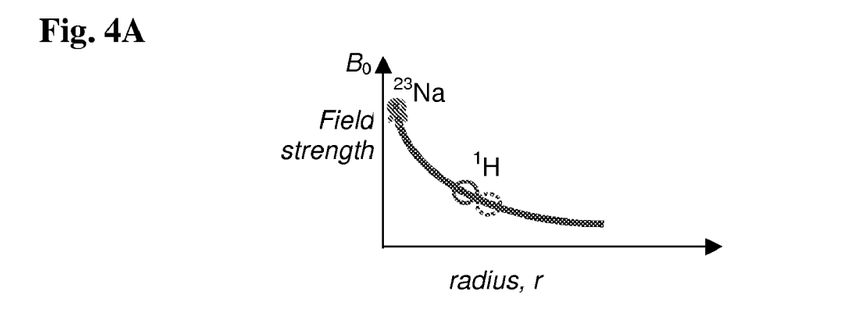
FIG. 4A depicts the responses to a traditional gradient NMR logging instrument.

Generally, in the prior art, the NMR signal associated with $^{23}$Na may overlap with the NMR signal associated with protons for the same excitation, as illustrated in FIG. 4A, although the signal of the $^{23}$Na may be quite weak. Accordingly, shifting of the NMR frequency generally results in a similar signal for the $^{23}$Na and H, as shown in the dotted line in FIG. 4A. This is exhibited as signal overlapping. Thus, the $^{23}$Na and H constituents are usually not well distinguished by use of different resonance frequencies.

Figure 4B:
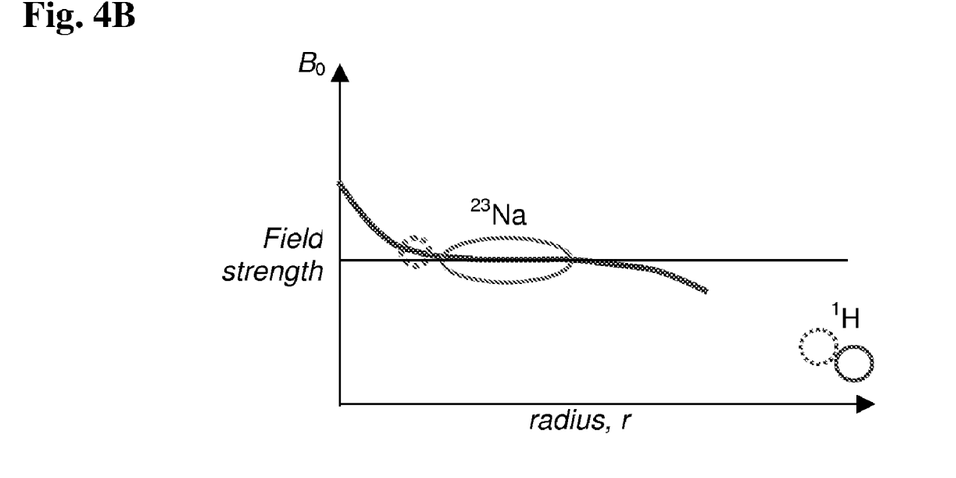
FIG. 4B depicts exemplary responses to a barrel shaped magnet.

However, using the barrel magnet configuration, if $^{23}$Na resonance frequency is set at the sweet spot, then the corresponding proton sensitive volume will be much deeper and much smaller, as shown in FIG. 4B. Accordingly, the signal for the proton is made very weak. This provides for resolving the $^{23}$Na signal. Furthermore, if the $^{23}$Na resonance frequency is slightly shifted away from the sweet spot, as shown in the dotted circles in FIG. 4B, the proton signal intensity corresponding to this second frequency is substantially the same but the $^{23}$Na signal will be substantially smaller than that on the sweet spot. Therefore, even if the proton signal overlaps with the $^{23}$Na signal, the proton component can be easily removed by computing the difference of the two frequency measurements.

Further techniques for diminishing the NMR signal associated with protons include use of fast measurement repetition. That is, because the NMR relaxation time of brine associated with $^{23}$Na is approximately 10 ms, one can set very short wait times, $T_w$, (normally three times the longitudinal relaxation time, $T_1$). However, light hydrocarbon has very long proton relaxation time, $T_1$. Accordingly, by using short wait times, $T_w$, the proton signal is underpolarized because of its longitudinal relaxation time, $T_1$. This results in further reducing unwanted contributions to the $^{23}$Na NMR signal.

A technique for separation of brine from hydrocarbon is now provided. In order to separate the hydrocarbon phase from the brine phase, two measurements are taken with NMR logging instruments. Two frequencies corresponding to the $^{23}$Na and $^{1}$H are tuned at the sweet spot of a static magnetic field. The two measurements are separately calibrated. Thus, the $^{23}$Na resonance frequency measurement acquires only the brine phase data, while the proton resonance frequency measurement acquires both the brine and hydrocarbon phase data. If the resonance frequency for $^{23}$Na is $f_{Na}$, the proton resonance at the same sensitive volume is substantially approximately $f_H = 3.7804 \cdot f_{Na}$.

In many cases, at least one of salinity and resistivity of formation water and mud filtrate is known. For example, knowledge may be obtained from a water sample test or from historical data for a given formation. In such cases, the $^{23}$Na signal strength can be converted to the volumetric quantity of brine when salinity is known. The difference between $^{1}$H-based volumetrics and $^{23}$Na-based volumetrics (porosity) is the hydrocarbon-bearing volume.

An application is also provided to determine the formation water resistivity, $R_w$. In the case where the formation water salinity is unknown, the measurement of $^{23}$Na in the water-bearing section can provide for determination of the formation water resistivity, $R_w$. That is, for a water-bearing section, the quantification of $^{23}$Na from Na NMR measurement and the porosity from proton NMR measurement, or other porosity measurement, such as density porosity, yields the reservoir or flushed-zone salinity determination. This quantity may be used for calculation of the formation water resistivity, $R_w$. Together with $R_t = R_o$ for water-saturated rock from induction or resistivity log measurement, and the porosity from proton NMR, one determines the cementation factor, m, and the porosity, $\phi$, using the Archie equation, provided as Eq. (1):

$$S_w = [(a/\phi^m)*(R_w/R_t)]^{(1/n)} \quad (1)$$

where:
$S_w$ represents water saturation;
$\phi$ represents porosity;
$R_w$ represents formation water resistivity;
$R_t$ represents observed bulk resistivity;

a represents a constant (often taken to be 1);
m represents a cementation factor (varies about 2); and,
n represents a saturation exponent (generally about 2).

For water based mud (WBM) filtrate flushed water-saturated zone, the salinity of brine, which is a mixture of filtrate and native reservoir brine, can be calculated from the $^{23}$Na NMR and porosity from proton NMR logs. Comparisons of these results with results of resistivity logging based $R_{xo}$ may be made for further insight into properties downhole. Some further aspects are now discussed with reference to FIG. 6.

Figure 6:
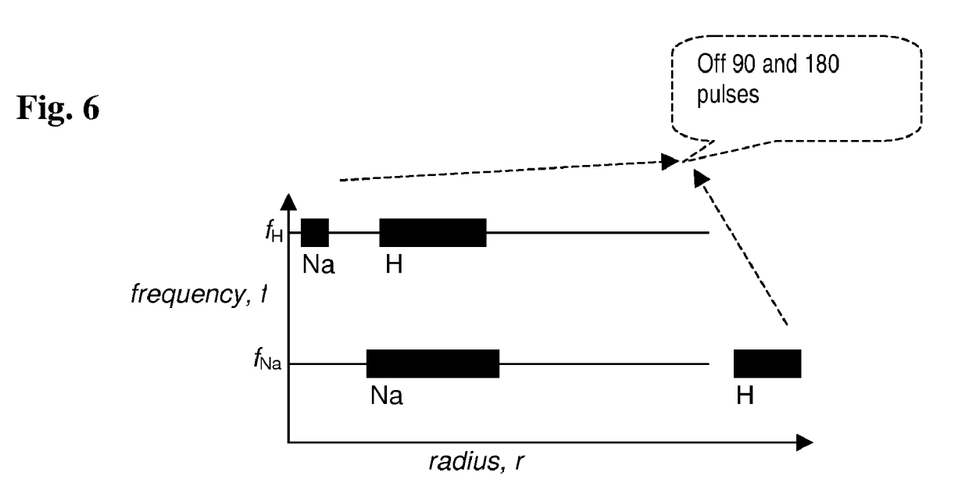
FIG. 6 depicts radius r, in relation to frequency.

Refer now to FIG. 6, where radius from a center of the wellbore 22, r, is shown as a function of frequency, f. At the frequency selected for sodium, $f_{Na}$, the proton signal is very weak and the sensitive volume is deep. At the frequency selected for hydrogen, $f_H$, the sodium 23 signal is small because sensitive volume is small due to large gradient.

As shown in FIG. 4B, the static field strength for the magnetic field, $B_0$, decreases rapidly to a plateau, and then again after the plateau (i.e., the "sweet spot"). In combination, it may be realized that slightly shifting the frequency used for sodium-23 causes the sodium signal intensity to decrease significantly, while the proton signal intensity remains approximately the same. This may be used to verify presence of sodium-23.

As the relaxation wait time, $T_w$, for sodium is relatively fast, while comparatively slow for the protons, certain advantages are realized. For example, short wait times may provide for a large repetition of measurements and improved reliability. This helps to further eliminate the proton signal and only require short echo trains. Further, there is little or no effect in the data from vibration of instrumentation (such as during drilling), and a simple CPMG sequence is realized.

Thus, certain advantages are realized. That is, for example, the teachings herein provide for, among other things, direct fluid typing. This is applicable to salt saturated or known salinity reservoirs, and may be performed using both $^{1}$H and $^{23}$Na measurements. More specifically, porosity may be determined by $^{1}$H NMR, water saturation by $^{23}$Na and then hydrocarbon content estimated by subtraction of the $^{23}$Na volume from the $^{1}$H volume. In addition, salinity variation measurements may be performed. This is particularly applicable to cases where $^{1}$H NMR is adequate for fluid typing. This provides for fluid typing (volumetrics) by use of the $^{1}$H NMR signal, and permits users to estimate quantities of injected (sea water) from connate (salt saturated or nearly saturated).

In support of the teachings herein, various analysis components may be used, including at least one of a digital system and an analog system. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a sample line, sample storage, sample chamber, sample exhaust, pump, piston, power supply (e.g., at least one of a generator, a remote supply and a battery), magnet, electromagnet, transmitter, receiver, transceiver, antenna, controller, electrical unit or electromechanical unit may be included in support of the various aspects discussed herein or in support of other functions beyond this disclosure.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for analytically separating properties of hydrocarbon materials from properties of non-hydrocarbon materials in an earth formation penetrated by a borehole using NMR relaxation times, the method comprising:

performing a first nuclear magnetic resonance (NMR) measurement for sodium-23 ($^{23}$Na) at a resonance frequency in a first sensitive volume in the earth formation outside of the borehole, using NMR relaxation times for the first sensitive volume that correlates to a relaxation time for the sodium-23 ($^{23}$Na), wherein the first sensitive volume has a homogeneous magnetic field having a magnetic field strength;

performing a second NMR measurement for hydrogen ($^{1}$H) at another resonance frequency in a second sensitive volume in the earth formation outside of the borehole, using NMR relaxation times for the second sensitive volume that correlates to a relaxation time for the hydrogen ($^{1}$H), wherein the second sensitive volume has a magnetic field gradient having a maximum magnetic field strength that is less than the magnetic field strength of the homogeneous magnetic field of the sodium-23 ($^{23}$Na);

wherein the first and second NMR measurements, respectively of sodium-23 ($^{23}$Na) and hydrogen ($^{1}$H), are performed with a magnet that comprises at least one of a barrel magnet, a bar magnet, and the combination of a barrel and bar magnet; and analytically separating the properties of the hydrocarbon materials from the properties of the non-hydrocarbon materials using the first sodium-23 ($^{23}$Na) NMR measurement and the second hydrogen ($^{1}$H), NMR measurement.

2. The method as in claim 1, further comprising determining properties of the non-hydrocarbon materials according to the sodium-23 ($^{23}$Na) signal.

3. The method as in claim 2, further comprising determining a volume of the non-hydrocarbon material.

4. The method as in claim 1, wherein the non-hydrocarbon materials comprise at least one of water, brine, salt water, drilling mud and mud filtrate.

5. The method as in claim 1, wherein the magnetization time for the first sensitive volume for sodium-23 ($^{23}$Na), is substantially shorter than a magnetization time of the second sensitive volume for protons hydrogen ($^{1}$H).

6. The method as in claim 1, wherein performing each of the first NMR measurements and the second NMR measurement comprises performing a series of repetitive measurements.

7. The method as in claim 1, wherein a measurement frequency for the sodium-23 ($^{23}$Na), is selected for shifting a resonance frequency of the sodium-23 ($^{23}$Na), away from a window of the homogeneous magnetic field, referred to as a "sweet spot."

8. The method as in claim 7, wherein the shifting comprises reducing an overlap of the sodium-23 ($^{23}$Na) NMR signals with an NMR signal for protons hydrogen ($^{1}$H).

9. The method as in claim 1, wherein the second sensitive volume for protons is substantially separate from the first sensitive volume for the sodium-23 ($^{23}$Na).

10. The method as in claim 1, wherein a magnetization time for the first NMR measurement sodium-23 ($^{23}$Na), is selected to underpolarize protons.

11. A non-transitory computer readable medium comprising instructions for analytically separating properties of hydrocarbon materials from non-hydrocarbon materials in an earth formation penetrated by a borehole, using NMR relaxation times, by implementing a method comprising:

performing a first nuclear magnetic resonance (NMR) measurement for sodium-23 ($^{23}$Na) at a resonance frequency in a first sensitive volume in the earth formation outside of the borehole, using NMR relaxation times for the first sensitive volume that correlates to a relaxation time for the sodium-23 ($^{23}$Na), wherein the first sensitive volume has a homogeneous magnetic field having a magnetic field strength;

performing a second NMR measurement for hydrogen (1H) at another resonance frequency in a second sensitive volume in the earth formation outside of the borehole, using NMR relaxation times for the second sensitive volume that correlates to a relaxation time for the hydrogen ($^{1}$H), wherein the second sensitive volume has a magnetic field gradient having a maximum magnetic field strength that is less than the magnetic field strength of the homogeneous magnetic field of the sodium-23 ($^{23}$Na);

wherein the first and second NMR measurements, respectively of sodium-23 ($^{23}$Na) and hydrogen ($^{1}$H), are performed with a magnet that comprises at least one of a barrel magnet, a bar magnet, and the combination of a barrel and bar magnet; and analytically separating the properties of the hydrocarbon materials from the properties of the non-hydrocarbon materials using the first sodium-23 ($^{23}$Na) NMR measurement and the second hydrogen ($^{1}$H), NMR measurement.

12. An apparatus configured for performing nuclear magnetic resonance (NMR) measurements in an earth formation penetrated by a borehole, using NMR relaxation times, the apparatus comprising:

a magnet comprising at least one of a barrel magnet, a bar magnet, and the combination of a barrel and bar magnet, that is configured to provide a homogeneous magnetic field having a magnetic field strength in a first sensitive volume in the earth formation outside of the borehole for obtaining a sodium-23 ($^{23}$Na), NMR response, using NMR relaxation times for the first sensitive volume that correlates to a relaxation time for the sodium-23 ($^{23}$Na), and a magnetic field gradient in a second sensitive volume in the earth formation outside of the borehole, using NMR relaxation times for the second sensitive volume that correlates to a relaxation time for the hydrogen ($^1$H), for obtaining a hydrogen (1H) NMR response, wherein a maximum magnetic field strength of the magnetic field gradient in the second sensitive volume is less than the magnetic field strength of the homogeneous magnetic field of the sodium-23 ($^{23}$Na).

13. A method for analytically separating properties of hydrocarbon materials from properties of non-hydrocarbon materials in an earth formation penetrated by a borehole, using NMR relaxation times, the method comprising:
performing a first nuclear magnetic resonance (NMR) measurement having a first magnetization time for sodium-23 ($^{23}$Na)) at a resonance frequency within a window of homogeneous magnetic field in the earth formation outside of the borehole using NMR relaxation times for the first sensitive volume that correlates to a relaxation time for the sodium-23 ($^{23}$Na);
performing a second nuclear magnetic resonance (NMR) measurement having a second magnetization time for hydrogen ($^1$H), at another resonance frequency within a window of homogeneous magnetic field in the earth formation outside of the borehole, using NMR relaxation times for the second sensitive volume that correlates to a relaxation time for the hydrogen ($^1$H);
wherein the first and second NMR measurements, respectively of sodium-23 ($^{23}$Na) and hydrogen ($^1$H), are performed with a magnet that comprises at least one of a barrel magnet, a bar magnet, and the combination of a barrel and bar magnet;
wherein the first magnetization time is less than the second magnetization time;
determining a signal for the sodium-23 ($^{23}$Na) from the first NMR measurement;
determining another signal for the hydrogen ($^1$H), and the sodium-23 ($^{23}$Na) from the second NMR measurement; and
separating the signal and the another signal to determine the properties of the hydrocarbon materials from the properties of the non-hydrocarbon materials.

14. A method for determining water saturation in a formation penetrated by a borehole, using NMR relaxation times, the method comprising:
performing a first nuclear magnetic resonance (NMR) measurement for sodium-23 ($^{23}$Na)) in a first sensitive volume in the formation outside of the borehole using NMR relaxation times for the first sensitive volume that correlates to a relaxation time for the sodium-23 ($^{23}$Na);
wherein the first sensitive volume has a homogeneous magnetic field having a magnetic field strength;
performing a second nuclear magnetic resonance (NMR) measurement for hydrogen ($^1$H), in a second sensitive volume in the formation outside of the borehole using NMR relaxation times for the second sensitive volume that correlates to a relaxation time for the hydrogen ($^1$H);
wherein the second sensitive volume has a magnetic field gradient having a maximum magnetic field strength that is less than the magnetic field strength of the homogeneous magnetic field of the sodium-23 ($^{23}$Na); with the hydrogen being related to the water in the formation and the sodium being related to the salt content of the water in the formation;
wherein the first and second NMR measurements, respectively of sodium-23 ($^{23}$Na) and hydrogen ($^1$H), are performed with a magnet that comprises at least one of a barrel magnet, a bar magnet, and the combination of a barrel and bar magnet; and
using a known salinity for the water, in order to determine the water saturation in the formation using the sodium-23 ($^{23}$Na) signal and the another hydrogen ($^1$H), signal.

15. The method as in claim 14, wherein the determining comprises solving the equation:

$$Sw=[(a/\phi^m)*(Rw/Rt)]^{(1/n)}$$ where:

water saturation;
$\phi$ represents porosity;
Rw represents formation water resistivity;
Rt represents observed bulk resistivity;
a represents a constant;
m represents a cementation factor; and,
n represents a saturation exponent.

16. The method as in claim 14, further comprising when Water saturation is known, solving the equation of claim 15, in order to determine a porosity of the formation from the first Sodium-23 ($^{23}$Na) and second hydrogen ($^1$H) proton NMR measurements.

17. The method as in claim 16, further comprising estimating a volume of hydrocarbon materials using the determined porosity and the known water saturation.

18. A method for determining salinity variation in a formation penetrated by a borehole using NMR relaxation times, when the oil and brine proton NMR response can be discerned from proton NMR measurements, the method comprising:
performing a sodium nuclear magnetic resonance (NMR) measurement in a first sensitive volume in the formation outside of the borehole using NMR relaxation times for the first sensitive volume that correlates to a relaxation time for the sodium; wherein the first sensitive volume has a homogeneous magnetic field having a magnetic field strength;
performing a proton nuclear magnetic resonance (NMR) measurement in a second sensitive volume in the formation outside of the borehole using NMR relaxation times for the second sensitive volume that correlates to a relaxation time of protons wherein the second sensitive volume has a magnetic field gradient having a maximum magnetic field strength that is less than the magnetic field strength of the homogeneous magnetic field of sodium;
wherein the first and second NMR measurements, respectively of sodium and hydrogen, are performed with a magnet that comprises at least one of a barrel magnet, bar magnet, and the combination of a barrel and bar magnet;
determining oil-filled and brine-filled porosity volumes separately with proton NMR parameters comprising at least one of a relaxation time, and a diffusivity;
determining a magnitude of a sodium-23 ($^{23}$Na); NMR signal which represents brine, where the sodium-23 ($^{23}$Na); NMR signal amplitude is pre-calibrated against a known salinity brine source;
determining the salinity of brine from a ratio of magnitude of sodium-23 ($^{23}$Na); signal and the brine filled porosity volume;
where a variation of salinity as a function of measured depth along the borehole is an indicator of at least one of a mud filtrate invasion change and the variation in native formation water salinity.

* * * * *